United States Patent
Fischer, Jr. et al.

(10) Patent No.: US 8,043,282 B2
(45) Date of Patent: Oct. 25, 2011

(54) DRAINAGE CATHETER WITH EXTENDED INFLATION LUMEN

(75) Inventors: Frank J. Fischer, Jr., Bloomington, IN (US); Tracy E. Willis, Bloomington, IN (US); Marvin O. Andrews, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 557 days.

(21) Appl. No.: 11/502,779

(22) Filed: Aug. 11, 2006

(65) Prior Publication Data
US 2007/0049907 A1    Mar. 1, 2007

Related U.S. Application Data

(60) Provisional application No. 60/708,014, filed on Aug. 12, 2005.

(51) Int. Cl.
*A61M 27/00* (2006.01)

(52) U.S. Cl. .................................................. 604/544

(58) Field of Classification Search .......... 604/540–544; 128/207.15
See application file for complete search history.

(56) References Cited

U.S. PATENT DOCUMENTS

| | | | |
|---|---|---|---|
| 4,429,856 A | 2/1984 | Jackson | |
| 4,501,580 A | 2/1985 | Glassman | |
| 4,515,593 A | 5/1985 | Norton | |
| 4,681,564 A * | 7/1987 | Landreneau | 604/128 |
| 4,932,938 A | 6/1990 | Goldberg et al. | |
| 5,041,092 A | 8/1991 | Barwick | |
| 5,306,226 A | 4/1994 | Salama | |
| 5,380,304 A | 1/1995 | Parker | |
| 5,700,253 A | 12/1997 | Parker | |
| 6,090,135 A * | 7/2000 | Plaia et al. | 623/1.11 |
| 6,979,313 B1 * | 12/2005 | Meek et al. | 604/98.01 |
| 2003/0153875 A1 | 8/2003 | Ostfeld et al. | |
| 2004/0039331 A1 * | 2/2004 | Coppi et al. | 604/101.04 |
| 2004/0181273 A1 * | 9/2004 | Brasington et al. | 623/1.15 |
| 2004/0215162 A1 | 10/2004 | Putz | |
| 2005/0143689 A1 * | 6/2005 | Ramsey, III | 604/103.13 |
| 2006/0090761 A1 | 5/2006 | Kurrus | |

FOREIGN PATENT DOCUMENTS

| | | |
|---|---|---|
| WO | WO 84/01513 | 4/1984 |
| WO | WO 93/04726 | 3/1993 |
| WO | WO 99/66976 | 12/1999 |

OTHER PUBLICATIONS

International Search Report from corresponding PCT application No. PCT/US2006/031577 dated Dec. 28, 2006 (6 pages).
International Preliminary Report of Patentability for related PCT application PCT/US2006/03157 dated Feb. 21, 2008.
Kaye Nephrostomy Tamponade Balloon [online], Apr. 2, 2007, [retrieved on Dec. 3, 2010], retrieved from http://www.cookmedical.com/uro/dataSheet.do?id=4088.
European Examination Report, issued in EP 06813407.1, dated Aug. 17, 2009.

* cited by examiner

*Primary Examiner* — Tatyana Zalukaeva
*Assistant Examiner* — Benedict L Hanrahan
(74) *Attorney, Agent, or Firm* — Brinks Hofer Gilson & Lione

(57) ABSTRACT

A Foley catheter with a retention balloon includes an elongated inflation tube so that the inflation port used to inflate and deflate the balloon may be maneuvered away from the drainage port of the Foley catheter. If the Foley catheter was placed using a urethral access sheath, the elongated inflation tube allows the surgeon to easily remove the access sheath from the patient.

8 Claims, 1 Drawing Sheet

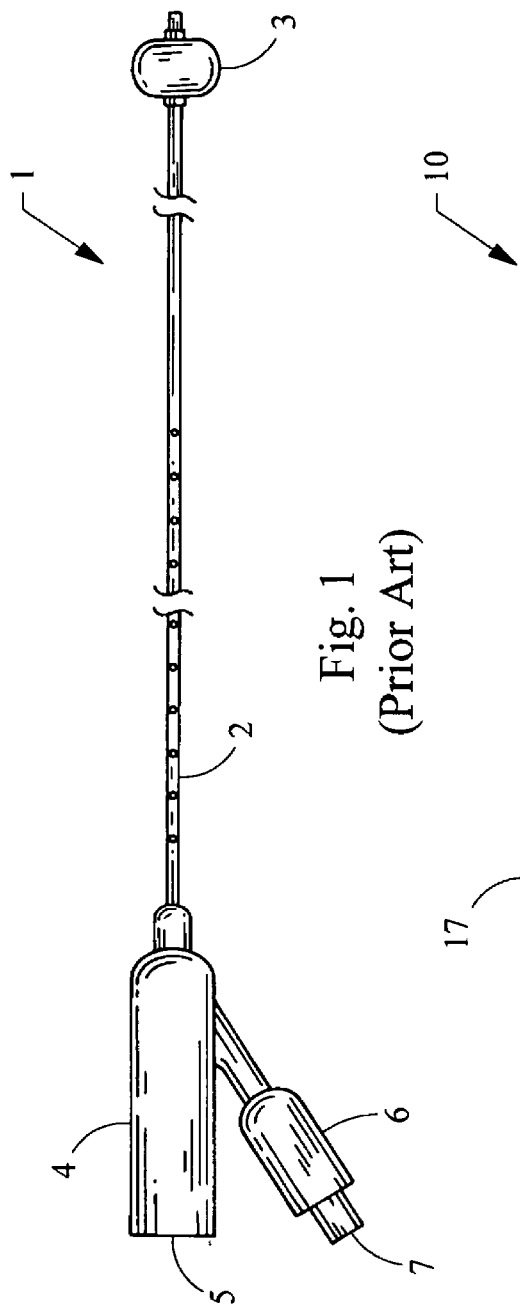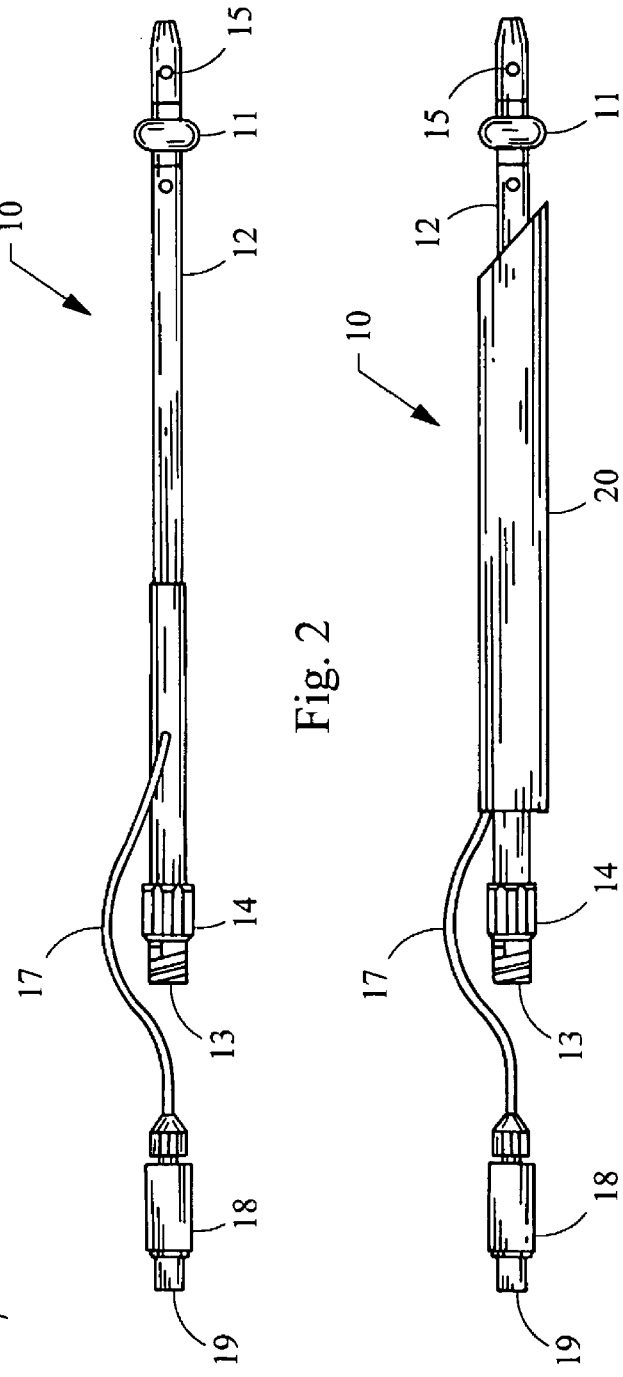

US 8,043,282 B2

DRAINAGE CATHETER WITH EXTENDED INFLATION LUMEN

RELATED APPLICATION

This application claims the benefit of priority from U.S. Provisional Patent Application Ser. No. 60/708,014, filed on Aug. 12, 2005, which is hereby incorporated by reference in its entirety.

FIELD OF THE INVENTION

The technical field of the invention is medical devices meant for implantation in a human or mammalian body, and in particular the technical field of drainage catheters intended for drainage of urine or other bodily fluids.

BACKGROUND

Drainage catheters are widely used when patients are unable to reliably void themselves, typically after surgery that is related to a urinary function. For men, the use of a drainage catheter may be related to surgery for a diseased prostrate gland. For women, a drainage catheter may be needed after surgery to repair the pelvic floor or to support the urethra. For patients of either sex, a urinary catheter may be needed when the patient is immobilized in a hospital bed. These catheters often take the form of what is known as a Foley catheter, which includes a drainage lumen from the bladder to outside the body.

A Foley catheter also includes a balloon placed in the urinary bladder for retention of the catheter. The balloon is inflated by using pressurized water or saline solution. The water or saline is added through an inflation lumen that is independent and separate from the drainage lumen. The inflation lumen extends from the balloon inside the bladder to a fitting outside the body. The fitting is used to inflate the balloon, which then holds the catheter reliably within the patient's urinary bladder.

In order to place the Foley catheter and the uninflated balloon into the patient's body, an access sheath is frequently used. An access sheath, such as one similar to those depicted in U.S. Pat. Nos. 5,380,304 and 5,700,253, assigned to the assignee of the present invention, is placed within the urethra. The catheter is then placed into the patient through the access sheath. The access sheath typically uses a very lubricious hydrophilic coating on its outside to ease the passage of the access sheath through the urethra.

One difficulty in using access sheaths is that once the Foley catheter has been placed, it may be difficult to remove the access sheath, because the proximal (outside) end of the Foley, with its fittings may be too wide to allow removal of the access sheath. Accordingly, access sheaths, such as those described in WIPO Publication No. WO 93/04726, have now been designed as "tear-away" sheaths, that is, they are easy to split along their entire length. Thus, the access sheath may be torn down its length and removed from the patient at will.

A problem with this approach is that, even with hydrophilic coatings, the process of tearing and removal of the access sheath is traumatic to the patient. What is needed is a Foley catheter that allows removal of the access sheath with a minimum of trauma to the patient. What is needed is a Foley catheter that can be implanted with the aid of an access sheath, and which allows removal of the access sheath once the Foley catheter is implanted.

BRIEF SUMMARY

One embodiment of the invention is a Foley catheter for insertion into a patient. The Foley catheter includes an elongated linear member with an external, proximal end comprising a drainage tube, a retention balloon on a distal end of the linear member for retaining the catheter within a hollow body part, and an inflation tube independent from the drainage tube, the inflation tube comprising an inflation lumen within the elongated linear member extending to the retention balloon on a distal end of the inflation lumen, the inflation tube also extending sufficiently beyond the proximal end of the elongated linear member that an access sheath used for placing the Foley catheter may be removed without splitting the access sheath.

Another aspect of the invention is a method of placing a Foley catheter within a patient. The method includes steps of placing an access sheath through a urethra of a patient, placing a Foley catheter through the access sheath so that a distal end and a retention balloon of the Foley catheter is placed within a body cavity of the patient, and maneuvering an inflation tube of the Foley catheter so that the access sheath may be removed from the patient without splitting the access sheath.

BRIEF DESCRIPTION OF THE DRAWINGS

FIG. 1 is a plan view of a prior art Foley catheter;
FIG. 2 depicts an embodiment of the present invention; and
FIG. 3 depicts use of the improved Foley catheter and how an access sheath may be removed from the patient while the Foley catheter remains.

DETAILED DESCRIPTION OF THE DRAWINGS AND THE PRESENTLY PREFERRED EMBODIMENTS

There are many embodiments of the present invention, a few of which will be described below. FIG. 1 depicts a prior art Foley catheter intended for placement in the bladder of a patient for drainage of urine. Foley catheter 1 includes a longitudinal body 2 having a retention balloon 3 at the distal end of the catheter and a drainage port 4 at the proximal end of the catheter. There is a drainage lumen 5 along the length of the catheter. The catheter may be open at its distal end to allow urine to enter drainage lumen 5, or the catheter may have ports or orifices at the distal end to allow urine to enter the catheter.

Foley catheter 1 is retained within the patient through balloon 3. The catheter is placed within the bladder of the patient, and is retained by inflating balloon 3. The balloon is inflated with several cc of saline or other medically acceptable fluid through inflation port 6 and inflation lumen 7. Inflation lumen 7 extends from port 6 through the length of the catheter body and into balloon 3. The inflation lumen may run parallel with the drainage lumen, but the two are kept separate for their entire lengths.

The Foley catheter may be placed into the patient by a procedure that gradually expands the urethra for easier passage of the Foley through the urethra and into the bladder. The procedure may involve passing a guidewire with a thin diameter through the urethra. After the guide wire is placed, a catheter with a larger diameter may be placed by running the catheter over the guidewire. An access sheath of 12-14 Fr. may then be placed over the catheter and may be run along the catheter and into the bladder. The catheter and guide wire are then removed from the patient. The access sheath is sufficiently large so that the Foley may be placed by simply inserting the Foley through the access sheath.

The difficulty, as mentioned above, comes in removing the sheath after the Foley catheter is placed. As FIG. 1 shows, the drainage port 4 and the inflation port 6 may have a considerable width or girth dimension. This does not concern the surgeon when placing the Foley into the patient, because only the uninflated balloon and the thin, longitudinal body of the catheter need to pass through the access sheath. However, when the access sheath itself is removed, the width of the ports prevents passage of the access sheath around the ports. Thus, access sheaths are now "splittable," i.e., they are manufactured with a line of perforations or thinned material along their length. When the surgeon wishes to remove the access sheath, he or she begins a tear at the proximal end of the access sheath. The tear then propagates along the weakened line and the sheath is split. The sheath can then be removed around the drainage and inflation ports.

This method, however, has disadvantages in that splitting and removing the sheath is somewhat painful for the patient, and, depending on the precise result of the tearing and splitting, may be traumatic to the patient. Embodiments of the invention avoid these difficulties by elongating the inflation lumen, and making sure that the diameters or girth dimensions of both the drainage port and the inflation port are sufficiently small that they may pass separately through the access sheath.

FIGS. 2 and 3 depict an embodiment of an improved Foley catheter. Foley catheter 10 includes a longitudinal body 12 with a drainage lumen 13 and a drainage port 14. Longitudinal body 12 has an outer diameter of 5.4 mm, although other sizes are contemplated depending on the needs of the patient. Drainage port 15 allows for fluid drainage from the dwelling area—such as the drainage of urine from the renal pelvis of the kidney; catheter 10 may optionally have more than one drainage port. Elongated inflation tube 17 is preferably 40-50 mm in length; however, other lengths are contemplated such that inflation tube 17 is long enough to allow the surgeon to manipulate inflation port 18 away from drainage port 14. Radiopaque markers (not shown) may optionally be located on longitudinal body 12 to aid in the positioning of catheter 10 using a fluoroscope or similar device. Catheter 10 is retained after placement in the bladder of a patient when inflation balloon 11 is inflated via inflation lumen 19 through inflation port 18 and an elongated inflation tube 17. Inflation balloon 11 preferably holds 5 cc of fluid; however, capacity to hold more or less fluid is contemplated depending upon the needs of the patient. Inflation lumen 19 preferably has an outer diameter of 0.9 mm-1.0 mm; however, other diameters are contemplated such that a fluid can travel therethrough to inflate inflation balloon 11. Drainage lumen 13 preferably has an outer diameter of 2.7 mm-2.8 mm; however, other diameters are contemplated such that a fluid can drain therethrough. Elongated inflation tube 17 allows the surgeon to manipulate inflation port 18 away from drainage port 14 so that the access sheath 20 may be first maneuvered around drainage port 14 and then inflation port 18. Catheter 10 is scalable for use with an access sheath of any size; its dimensions are alterable so that it may be appropriately dimensioned to navigate to the target cavity.

The advantage to the surgeon is that less skill is needed to tear the access sheath apart longitudinally for removal. The advantage to the patient is less trauma than when the sheath is torn and removed.

Besides access to the bladder, embodiments of the present invention are equally useful in gaining access for directly draining a kidney and other cavities or hollow body parts of a patient. In this procedure, access to the renal calices of the kidney is gained through percutaneous application of a needle and a wireguide. The space, for example, is dilated to 26 or 30 Fr. and an access sheath of up to 30 Fr., for example, is then placed into the kidney to serve as an access channel. A procedure may then be performed, such as removing calculi, using the sheath. Afterwards, an improved Foley catheter 10 may then be placed using the sheath. Notably, catheter 10 is not limited to use with a 30 Fr. access sheath; instead, catheter 10 can be scaled for use with an access sheath having any size. The sheath is then removed without having to split or tear the sheath, the procedure made much easier with the elongated inflation lumen 19 of the improved Foley catheter 10. Besides this procedure for a percutaneous nephrostomy, an improved Foley catheter 10 may also be used for percutaneous or minimally-invasive procedures. These procedures may include, but are not limited to, suprapubic urinary bladder drainage, gall bladder drainage, hepatic drainage, and bowel drainage procedures.

It is intended that the foregoing detailed description be regarded as illustrative rather than limiting, and that it be understood that it is the following claims, including all equivalents, that are intended to define the spirit and scope of this invention.

The invention claimed is:

1. A method of placing a Foley catheter within a patient, the method comprising:
   placing an access sheath through a urethra of a patient, wherein access to the urethra is obtained through a natural body passage, the access sheath having a proximal end and a distal end and having a length that enables the distal end of the access sheath to gain access to a body cavity while the proximal end of the access sheath is exterior to the patient;
   placing a Foley catheter through the access sheath so that a distal end and a retention balloon of the Foley catheter is placed within a body cavity of the patient; and
   maneuvering an inflation tube of the Foley catheter so that the access sheath may be removed from the patient without splitting the access sheath, whereby the catheter remains inserted in the patient while the access sheath is being removed.

2. The method of claim 1, wherein the catheter comprises:
   an elongated linear member with an external, proximal end comprising a drainage lumen;
   a retention balloon on a distal end of the linear member for retaining the catheter within a hollow body part;
   a removable access sheath for placing the Foley catheter, the access sheath having a proximal end and a distal end and having a length that enables the distal end of the access sheath to gain access to the hollow body part while the proximal end of the access sheath is exterior to the patient; and
   an inflation tube independent from the drainage lumen, the inflation tube comprising an inflation lumen within the elongated linear member extending to the retention balloon on a distal end of the inflation lumen, the inflation tube also extending sufficiently beyond the proximal end of the elongated linear member that the access sheath may be removed without splitting the access sheath.

3. The method of claim 2, wherein the inflation tube is at least partly contained in a separate tube with an inflation fitting, the inflation fitting having a diameter narrower than that of the access sheath.

4. The method of claim 2, wherein the inflation tube and the linear member containing the drainage lumen are configured so that the access sheath is removable without splitting.

5. The method of claim 2, wherein the catheter further comprises a normally-closed inflation fitting on a proximal end of the inflation tube.

6. The method of claim 2, wherein the catheter further comprises a plug on the end of the inflation tube, the plug holding the inflation lumen closed.

7. The method of claim 2, wherein the catheter further comprises a wire guide for placing the Foley catheter.

8. The method of claim 2, wherein the catheter further comprises at least one radiopaque marker attached to the elongated linear member.

* * * * *